(12) United States Patent
Flamand et al.

(10) Patent No.: US 11,501,661 B2
(45) Date of Patent: Nov. 15, 2022

(54) METHOD AND SYSTEM FOR SIMULATING AN INSERTION OF AN ELONGATED INSTRUMENT INTO A SUBJECT

(71) Applicant: CAE HEALTHCARE CANADA INC., Saint-Laurent (CA)

(72) Inventors: Jean-Sébastien Flamand, Saint-Laurent (CA); Francois Caron, Saint-Laurent (CA)

(73) Assignee: CAE HEALTHCARE CANADA INC., Saint-Laurent (CA)

( * ) Notice: Subject to any disclaimer, the term of this patent is extended or adjusted under 35 U.S.C. 154(b) by 376 days.

(21) Appl. No.: 15/976,047

(22) Filed: May 10, 2018

(65) Prior Publication Data

US 2019/0304344 A1   Oct. 3, 2019

(30) Foreign Application Priority Data

Mar. 29, 2018   (CA) ................................ CA 3000164

(51) Int. Cl.
 *G09B 23/28*   (2006.01)
 *A61B 34/10*   (2016.01)
 *G09B 9/00*    (2006.01)
(52) U.S. Cl.
 CPC ............ *G09B 23/285* (2013.01); *A61B 34/10* (2016.02); *G09B 9/00* (2013.01); *A61B 2034/101* (2016.02)
(58) Field of Classification Search
 CPC ....... G09B 23/28; G09B 23/286; G09B 23/30
 (Continued)

(56) References Cited

U.S. PATENT DOCUMENTS

| 4,907,973 | A | * | 3/1990 | Hon ..................... G09B 23/285 434/262 |
| 6,024,576 | A | * | 2/2000 | Bevirt ..................... G05G 9/04 345/158 |

(Continued)

FOREIGN PATENT DOCUMENTS

CA   2921848 A1   4/2016

OTHER PUBLICATIONS

Korzeniowski Przemyslaw et al., "NOViSE: A Virtual Natural Orifice Transluminal Endoscopic Surgery Simulator", International Journal of Computer Assisted Radiology and Surgery, Springer, DE, vol. 11, No. 12, Jun. 17, 2016, pp. 2303-2315.

*Primary Examiner* — Kurt Fernstrom
(74) *Attorney, Agent, or Firm* — Fasken Martineau Dumoulin LLP; Serge Lapointe

(57) ABSTRACT

A method for simulating an insertion of an elongated instrument into a subject, the method comprising: receiving one of an actual angular position and a rotation angle for a proximal section of the elongated instrument, at least a distal end of the elongated instrument being inserted into a medical apparatus; determining a distal angular position for the distal end of the elongated instrument inserted into the medical apparatus using an adjustment factor and the one of the actual angular position and the rotation angle for the proximal section of the elongated instrument; generating a medical image of at least a portion of the subject, the medical image comprising at least a representation of a distal section of the elongated instrument, the representation of the distal section being generated according to the distal angular position; and outputting the generated medical image.

22 Claims, 6 Drawing Sheets

(58) Field of Classification Search
USPC .................................... 434/262, 267, 272
See application file for complete search history.

(56) References Cited

U.S. PATENT DOCUMENTS

| | | | |
|---|---|---|---|
| 6,902,405 B2* | 6/2005 | Irion | G05G 9/047 |
| | | | 434/262 |
| 6,939,138 B2* | 9/2005 | Chosack | G06T 15/00 |
| | | | 434/262 |
| 7,144,378 B2 | 12/2006 | Arnott | |
| 7,520,749 B2* | 4/2009 | Ohlsson | G09B 23/285 |
| | | | 434/262 |
| 7,806,696 B2* | 10/2010 | Alexander | G09B 23/285 |
| | | | 434/262 |
| 8,157,567 B2* | 4/2012 | Chen | G09B 23/285 |
| | | | 434/262 |
| 8,216,255 B2 | 7/2012 | Smith et al. | |
| 8,485,829 B2* | 7/2013 | Cusano | G09B 23/30 |
| | | | 345/156 |
| 8,696,363 B2* | 4/2014 | Gray | G09B 23/285 |
| | | | 434/262 |
| 8,974,401 B2 | 3/2015 | Taylor | |
| 9,084,558 B2 | 7/2015 | Furbush, Jr. | |
| 9,439,653 B2 | 9/2016 | Avneri et al. | |
| 9,711,066 B2 | 7/2017 | Van Dinther | |
| 10,134,306 B2* | 11/2018 | Lavigueur | G09B 23/28 |
| 2004/0076940 A1 | 4/2004 | Alexander et al. | |
| 2007/0134637 A1 | 6/2007 | Bronstein et al. | |
| 2007/0166682 A1* | 7/2007 | Yarin | G09B 23/285 |
| | | | 434/267 |
| 2009/0076417 A1 | 3/2009 | Jones | |
| 2009/0263775 A1 | 10/2009 | Ullrich | |
| 2010/0100103 A1 | 4/2010 | Haskal et al. | |
| 2010/0234873 A1 | 9/2010 | Nagano et al. | |
| 2015/0057575 A1 | 2/2015 | Tsusaka et al. | |
| 2015/0086958 A1* | 3/2015 | Lewis | G09B 23/288 |
| | | | 434/267 |
| 2015/0206456 A1* | 7/2015 | Foster | G09B 23/30 |
| | | | 434/262 |
| 2015/0335860 A1 | 11/2015 | Klocke et al. | |
| 2016/0114139 A1 | 4/2016 | McArthur et al. | |
| 2017/0035995 A1 | 2/2017 | Shevgoor et al. | |

\* cited by examiner

METHOD AND SYSTEM FOR SIMULATING AN INSERTION OF AN ELONGATED INSTRUMENT INTO A SUBJECT

TECHNICAL FIELD

The invention relates to medical simulation systems and methods, and more particularly to systems and methods for simulating the insertion of an elongated instrument into a subject.

BACKGROUND

Minimally invasive surgical procedures through the use of surgical instruments are more and more used for replacing conventional surgery. Indeed, the technological progress has provided miniaturized tools and implements that can be inserted through a surgical instrument, such as a catheter, in a subject for performing various tasks. These tools are generally combined with a video system to view from the inside the procedure being performed.

Virtual simulation systems have been developed for training medical professionals to perform these types of procedures. These simulation systems aim to produce realistic simulated operating conditions for providing interactive training through the combination of a hardware component and a visual representation returned to the medical professional under training.

However, these systems may be unrealistic and may generate an inaccurate visual representation of the surgical procedure for the medical professional under training. For instance, detecting and determining the longitudinal position and the angular position of a surgical instrument such as a catheter or a guidewire inserted within a subject may be challenging. Indeed, the characteristics of the subject's body such as the diameter of an artery into which the surgical instrument is inserted or the viscosity of the blood present therein may cause potential buckling and/or twisting of the surgical instrument which may not be taken into account during the simulation. The bucking and/or twisting may further be increased by the use of thin surgical instruments.

There is therefore a need for an improved method and system for simulating the insertion of an elongated instrument into a subject.

SUMMARY

According to a first broad aspect, there is provided a system for simulating an insertion of an elongated instrument into a subject, the system comprising: a medical apparatus comprising a frame extending between a proximal face and a distal face along a longitudinal axis, the proximal face being provided with an aperture for receiving the elongated instrument therein; a sensing unit being configured to measure one of an actual angular position and a rotation angle for a proximal section of the elongated instrument, the proximal section of the elongated instrument being outside of the medical apparatus; and a simulation machine in communication with the sensing unit for receiving the measured angular position therefrom, the simulation machine comprising at least a processing unit configured for: calculating a distal angular position for a distal end of the elongated instrument using an adjustment factor and the one of the actual angular position and the rotation angle for a proximal section of the elongated instrument; generating a medical image of at least a portion of the subject, the medical image comprising at least a representation of a distal section of the elongated instrument, the representation of the distal section being generated according to the distal angular position; and outputting the generated medical image.

In one embodiment, the sensing unit is adapted to measure actual angular position of the proximal section of the elongated instrument, the processing unit being further configured for determining the rotation angle based on the actual angular position and an initial angular position.

In one embodiment, the sensing unit is securable to the proximal section of the elongated instrument.

In one embodiment, the sensing unit comprises a tubular section securable over a portion of the proximal section of the elongated instrument.

In one embodiment, the sensing unit comprises a first hemi-tubular section and a second hemi-tubular section securable together over the elongated instrument.

In one embodiment, the first hemi-tubular section and the second hemi-tubular section of the sensing unit are hingedly secured together.

In one embodiment, the sensing unit comprises at least one gyroscope sensor for measuring the one of the actual angular position and the rotation angle for the proximal section of the elongated instrument.

In one embodiment, the sensing unit is further configured for measuring one of an actual longitudinal position and a longitudinal displacement for the proximal section of the elongated instrument, the processing unit being further configured for: calculating a distal longitudinal position for the distal end of the elongated instrument using a correction factor and the one of the actual longitudinal position and the longitudinal displacement for the proximal section of the elongated instrument; and generating the medical image taking into account the distal longitudinal position for the distal end of the elongated instrument.

In one embodiment, the sensing unit is configured for measuring the actual longitudinal position of the proximal section of the elongated instrument and the processing unit is further configured for determining the longitudinal displacement for the proximal section of the elongated instrument using the actual longitudinal position and an initial longitudinal position for the proximal section of the elongated instrument.

In one embodiment, the sensing unit further comprises at least one accelerometer for measuring the one of the actual longitudinal position and the longitudinal displacement for the proximal section of the elongated instrument.

In one embodiment, the system further comprises the elongated instrument.

In one embodiment, the sensing unit is fixedly secured to the proximal section of the elongated instrument.

In one embodiment, the elongated instrument is selected from a group consisting of a catheter, a lead wire, a delivery tube and a guidewire.

In one embodiment, the medical apparatus further comprises a longitudinal guide secured within the frame, the longitudinal guide extending between the proximal face and the distal face along the longitudinal axis for receiving and guiding the distal end of the elongated instrument upon insertion through the aperture of the proximal face.

In one embodiment, the medical apparatus comprises a position sensor for measuring one of a longitudinal position and a displacement for the distal end of the elongated instrument within the frame.

In one embodiment, the processing unit is configured for at least one of storing the generated medical image into a memory and transmitting the generated medical image to a display unit to be displayed thereon.

In one embodiment, the sensing unit comprises a wireless communication unit for wirelessly transmitting at least the measured angular position to the simulation machine.

According to another broad aspect, there is provided a computer-implemented method for simulating an insertion of an elongated instrument into a subject, the method comprising: receiving one of an actual angular position and a rotation angle for a proximal section of the elongated instrument, at least a distal end of the elongated instrument being inserted into a medical apparatus; determining a distal angular position for the distal end of the elongated instrument inserted into the medical apparatus using an adjustment factor and the one of the actual angular position and the rotation angle for the proximal section of the elongated instrument; generating a medical image of at least a portion of the subject, the medical image comprising at least a representation of a distal section of the elongated instrument, the representation of the distal section being generated according to the distal angular position; and outputting the generated medical image.

In one embodiment, said receiving the one of the actual angular position and the rotation angle comprises receiving the actual angular position of the proximal section of the elongated instrument, the method further comprising determining the rotation angle using the actual angular position and an initial angular position for proximal section of the elongated instrument.

In one embodiment, the method further comprises receiving one of an actual longitudinal position and a longitudinal displacement for the proximal section of the elongated instrument and calculating a distal longitudinal position for the distal end of the elongated instrument using a correction factor and the one of the actual longitudinal position and the longitudinal displacement for the proximal section of the elongated instrument; said generating the medical image being performed taking into account the distal longitudinal position for the distal end of the elongated instrument.

In one embodiment, said receiving the one of the actual longitudinal position and the longitudinal displacement comprises receiving the actual longitudinal position, the computer-implemented method further comprising determining the longitudinal displacement for the proximal section of the elongated instrument using the actual longitudinal position and an initial longitudinal position for the proximal section of the elongated instrument.

In one embodiment, said receiving the one of the actual angular position and the rotation angle comprises at least one acceleration value.

In one embodiment, the method further comprises determining the one of the actual angular position and the rotation angle from the at least one acceleration value.

In one embodiment, said receiving the one of the actual angular position and the rotation angle, determining the distal angular position, generating the medical image and outputting the generated medical image are performed substantially in real time.

In one embodiment, the method further comprises displaying the generated image on a display unit.

In one embodiment, a value of the adjustment factor depends on a position of the distal end of the elongated instrument within the medical apparatus.

It should be understood that the subject may be a human being, an animal or the like.

In one embodiment, a value of the correction factor depends on the position of the distal end of the elongated instrument within the medical apparatus.

BRIEF DESCRIPTION OF THE DRAWINGS

Having thus generally described the nature of the invention, reference will now be made to the accompanying drawings, showing by way of illustration example embodiments thereof and in which.

DETAILED DESCRIPTION

In the following, there is described a simulation system for simulating the insertion of an elongated instrument into a subject that may occur during a surgery procedure for example. There is also described a computer-implemented method for simulating the insertion of the elongated instrument into the subject.

In one embodiment, the simulation system provides a realistic and comprehensive training environment for diagnostics and the acquisition of basic surgical skills such as the maneuvering of surgical instruments for medical practitioner trainees. The system therefore provides hands-on practice for medical practitioner trainees in order to improve their technique prior to surgery on a patient.

Figure 1:
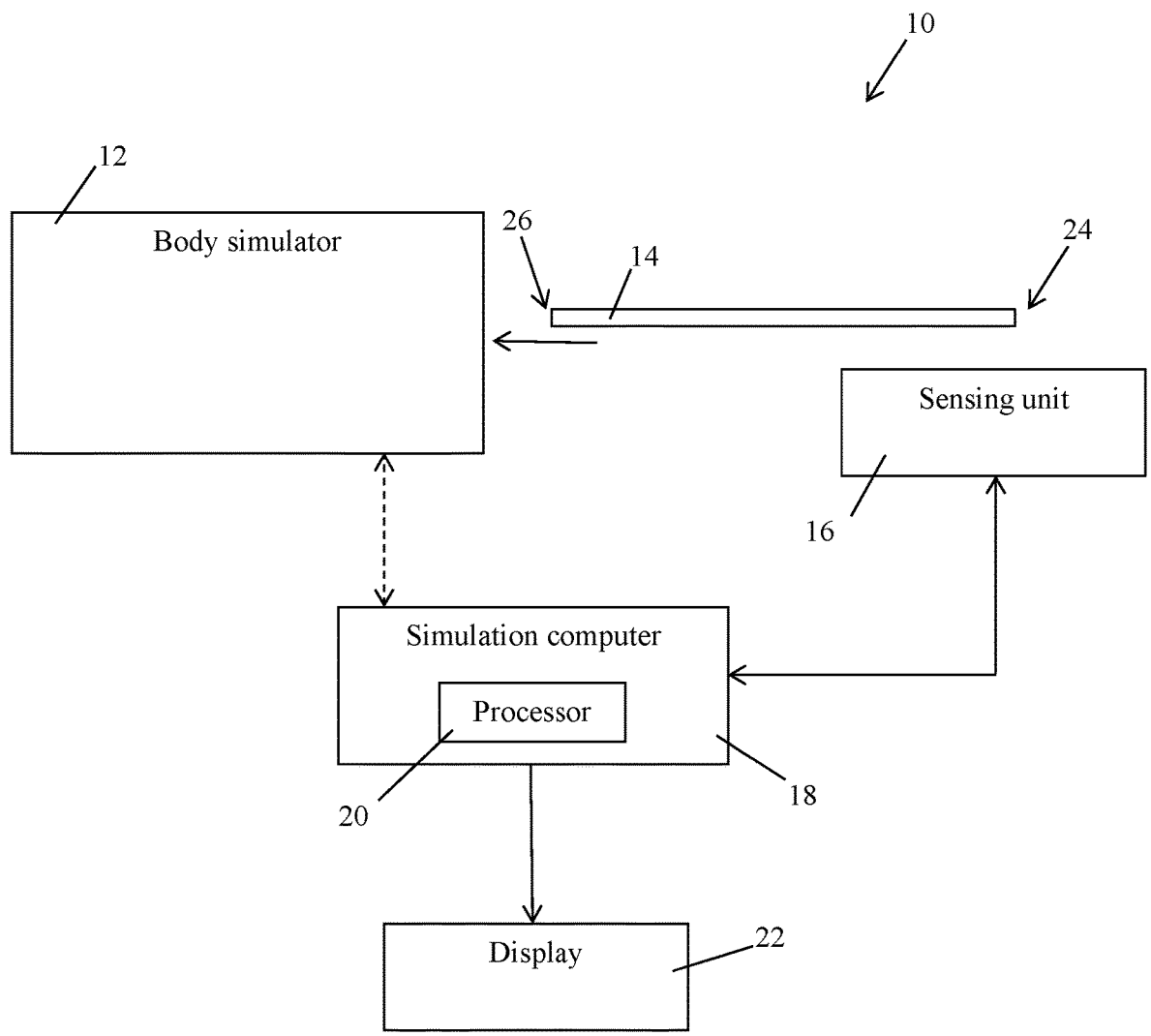
FIG. 1 is a block diagram illustrating a system comprising a sensing unit, an elongated instrument, an apparatus, a simulation machine and a display unit for simulating the insertion of the elongated instrument into a subject, in accordance with a first embodiment.

FIG. 1 illustrates one embodiment of a system 10 for simulating the insertion of an instrument into a subject. The system 10 comprises a medical or body simulating apparatus 12, an elongated medical instrument 14 insertable at least partially into the medical apparatus 12, a sensing unit 16, a simulation computer machine 18 provided at least with a processing unit 20 configured for generating medical images, and a display unit 22 for displaying the generated medical images thereon.

The medical apparatus 12 comprises a frame provided with at least one aperture shaped and sized so that the elongated instrument 14 may be inserted therethrough. In one embodiment, the frame is hollow so that at least a portion of the elongated instrument 14 may be inserted in the medical apparatus 12. In another embodiment, the medical apparatus 12 comprises at least a chamber of cavity in which the elongated instrument 16 may be at least partially inserted. As described below, the medical apparatus 12 may comprise further internal components positioned within the frame.

The elongated instrument 14 extends between a proximal end 24 and a distal end 16 along a longitudinal axis and may have any adequate elongated shape as a long as at least a distal section of the elongated instrument 14 is insertable into the medical apparatus 12. For example, the elongated instrument 14 may have a cylindrical or tubular shape. In another example, the elongated instrument 14 may have a hollow oval cross-sectional shape, a square cross-sectional shape, etc. In one embodiment, the elongated instrument 14 is a real medical instrument that may be used during a real medical procedure. In another embodiment, the elongated instrument 14 may be a mock-up elongated instrument mimicking a real medical instrument. For example, the elongated instrument may be a real or mock-up guidewire, lead cable or wire, catheter, delivery tube, or the like.

The sensing unit 16 is configured for determining the angular position and/or a rotation angle of the proximal section of the elongated instrument 14. It should be understood that the rotation of the elongated instrument 14 refers to the rotation of the elongated instrument 14 along its longitudinal axis.

In one embodiment, the proximal section of the elongated instrument 14 corresponds to the section of the elongated instrument 14 that is outside of the medical apparatus 12 when at least the distal end 26 of the elongated instrument 14 is inserted into the medical apparatus 12. In another embodiment, the proximal section of the elongated instrument 14 is adjacent to the proximal end 24 of the elongated instrument 14. In a further embodiment, the proximal section of the elongated instrument corresponds to the section of the elongated instrument 14 that is hold and manipulated by the user during the insertion of the distal end 26 of the elongated instrument 14 inside the medical apparatus 12.

In one embodiment, measuring the rotation angle or angular position of the proximal end 24 is equivalent to measuring the rotation angle or angular position of the proximal section of the elongated instrument 14.

In one embodiment, the sensing unit 16 is further configured for determining the longitudinal displacement or translation of the proximal section along the longitudinal axis of proximal section of the elongated instrument 14, or the longitudinal position of the proximal section of the elongated instrument 14. In one embodiment, the longitudinal position or displacement of the proximal section may be obtained by measuring the longitudinal position or displacement of the proximal end 24 of the elongated instrument 14.

In one embodiment, the sensing unit 16 is configured for remotely determining the angular position or the rotation angle of the proximal section of the elongated instrument 14, and optionally the longitudinal displacement or the longitudinal position of the proximal section of the elongated instrument 14. For example, the elongated instrument may be provided with reference marks or elements removably or fixedly secured to its proximal section and the sensing unit 16 may be configured for detecting the 3D position of the reference elements and determine the angular position or the rotation angle of the proximal section of the elongated instrument 14, and optionally the longitudinal displacement or the longitudinal position of the proximal section of the elongated instrument 14, based on the 3D position of the reference elements.

In another embodiment, the sensing unit 16 may be removably or fixedly secured to the proximal section of the elongated instrument 14. It should be understood that the sensing unit 16 may comprise any adequate sensor or combination of sensors adapted to measure the angular position of the proximal section of the elongated instrument 14 or the rotation of the proximal section of the elongated instrument 14 about its longitudinal axis. For example, the sensing unit 16 may comprise at least one gyroscope, at least one gyrometer, at least two accelerometers, at least one compass sensor or any combination thereof, to measure the angular position or the rotation angle of the proximal section of the elongated instrument 14. Optionally, the sensing unit 16 may include at least one accelerometer for determining the longitudinal position or displacement of the proximal section of the elongated instrument 14.

It should be understood that the determination of the rotation angle, the angular position, the longitudinal position and/or the longitudinal displacement of the proximal section of the elongated instrument can be done at a specific reference point along the proximal section of the elongated instrument 14. For example, the reference point may be the proximal end 24 of the elongated instrument. In another example, the reference point may be any point located on the lateral surface of the elongated instrument 14 adjacent to the proximal end 24 as along as the reference point is not inserted into the medical apparatus 12.

It should be understood that the sensing unit 14 is provided with communication means for transmitting the measured values.

The sensing unit 16 is in communication with the simulation computer machine 18. For example, a communication wire may connect the sensing unit 16 and the simulation computer 18 together. Alternatively, the sensing unit 16 may wirelessly communicate with the simulation computer machine 18.

The simulation computer machine 18 comprises a processing unit 20, a memory for storing data thereon and a communication unit for receiving and transmitting data. The measured angular position or the rotation angle measured by the sensing unit 16 is received by the simulation computer machine 18 from the sensing unit 16. The processing unit 20 is configured to determine the angular position of the distal end 26 of the elongated member 14 inserted into the medical apparatus 12 using the angular position or the rotation angle received from the sensing unit 16 and an adjustment factor. Furthermore, the processing unit 20 of the simulation computer machine 18 is configured to generate a simulated medical image which comprises a representation of a portion of the subject and a representation of at least the distal end of the elongated instrument 26. The representation of the distal end 16 of the elongated instrument 14 is generated according to the determined angular position of the distal end 26 so that the orientation of the distal end of the simulated elongated instrument correspond to the actual angular position of the distal end 26 of the elongated instrument 14 within the medical apparatus 12.

The processing unit 20 of the simulation computer machine 18 is further configured for outputting the generated medical image. In one embodiment, the generated medical image is outputted. In the same or another embodiment, the generated medical image is sent to the display unit 22 to be displayed thereon.

In one embodiment, the processing unit 20 of the simulation computer machine 18 is further configured for determining the longitudinal position of the distal end 26 of the elongated instrument 14 using a correction factor and the longitudinal position or displacement measured by the sensing unit 26.

In an embodiment in which the sensing unit 16 is configured for measuring the rotation angle of the proximal section of the elongated member 14, the processing unit 20 of the simulation computer machine 18 is configured for determining the angular position of the distal end of the elongated instrument 14 using the adjustment factor and the measured rotation angle of the proximal section of the elongated member 14. For example, the measured rotation angle of the proximal section of the elongated member 14 may be multiplied by the adjustment factor to obtain the rotation angle to be applied to the distal end 26 of the elongated instrument 14 located within the medical apparatus 12. The actual angular position for the distal end 26 of the elongated instrument 14 is determined using the determined rotation angle for the distal end 26 of the elongated instrument and the initial angular position of the distal end 26 of the elongated instrument 14, i.e. the determined rotation angle for the distal end 26 is added to the initial angular position of the distal end 26.

In an embodiment in which the sensing unit 16 is configured for measuring the actual angular position of the proximal section of the elongated instrument 14, the processing unit 20 of the simulation computer machine 18 is configured for determining the rotation angle of the proximal section of the elongated member 14 by comparing the actual angular position of the proximal section to the previous to the previous or initial angular position of the proximal section. Once the rotation angle of the proximal section has been determined, the processing unit 20 of the simulation computer machine 18 calculates the corresponding rotation angle for the distal end 26 of the elongated instrument using the adjustment factor and the determined rotation angle of the proximal section of the elongated instrument 14. For example, the rotation angle determined for the proximal section of the elongated member 14 may be multiplied by the adjustment factor to obtain the rotation angle to be applied to the distal end 26 of the elongated instrument 14 located within the medical apparatus 12. The actual angular position for the distal end 16 of the elongated instrument 14 is determined using the determined rotation angle for the distal end 26 of the elongated instrument and the previous or initial angular position of the distal end 26 of the elongated instrument 14, i.e. the determined rotation angle for the distal end 26 is added to the initial angular position of the distal end 26.

In one embodiment, the adjustment factor varies as a function of the length of the portion of the elongated instrument inserted into the medical apparatus 12 or the position of the distal end 26 of the elongated instrument 14 within the medical apparatus 12. It should be understood that the length of the portion of the elongated instrument inserted into the medical apparatus 12 corresponds to the distance between the distal end 26 of the elongated instrument 14, when inserted into the medical apparatus 12, and the aperture through which the elongated instrument 14 has been inserted into the medical apparatus 12.

In one embodiment, the adjustment factor may decrease with the length of the portion of the elongated instrument inserted into the medical apparatus 12. As a result, the farther the distal end 16 of the elongated instrument is inserted into the medical apparatus 12, the less the adjustment factor is. This scenario allows simulating an increase of the torsion of the elongated instrument 14 as the elongated instrument 14 is more and more deeply inserted into the medical apparatus 12.

In one embodiment, the memory of the simulation computer machine 18 comprises a database containing respective values for the adjustment factor for different positions of the distal end 26 of the elongated instrument 14 within the medical apparatus 12.

In an embodiment in which the sensing unit 16 is further configured for measuring the longitudinal displacement of the proximal section of the elongated instrument 14, the processing unit 20 of the simulation computer 18 is configured for determining the longitudinal position of the distal end 26 of the elongated instrument 14 using the correction factor and the measured longitudinal displacement of the proximal section of the elongated member 14. For example, the measured longitudinal displacement of the proximal section of the elongated member 14 may be multiplied by the correction factor to obtain the longitudinal displacement to be applied to the distal end 26 of the elongated instrument 14 located within the medical apparatus 12. The actual longitudinal position for the distal end 26 of the elongated instrument 14 is determined using the determined longitudinal displacement for the distal end 26 of the elongated instrument and the initial or previous longitudinal position of the distal end 26 of the elongated instrument 14, i.e. the determined longitudinal displacement for the distal end 26 is added to the previous longitudinal position of the distal end 26.

In an embodiment in which the sensing unit 16 is configured for measuring the actual longitudinal position of the proximal section of the elongated instrument 14, the processing unit 20 of the simulation computer machine 18 is configured for determining the longitudinal displacement of the proximal section of the elongated member 14 by comparing the actual longitudinal position of the proximal section to the initial or previous longitudinal position of the proximal section. Once the longitudinal displacement of the proximal section has been determined, the processing unit 20 of the simulation computer machine 18 calculates the corresponding longitudinal displacement for the distal end 26 of the elongated instrument 14 using the correction factor and the determined longitudinal displacement of the proximal section of the elongated instrument 14. For example, the longitudinal displacement determined for the proximal section of the elongated member 14 may be multiplied by the correction factor to obtain the longitudinal displacement to be applied to the distal end 26 of the elongated instrument 14 located within the medical apparatus 12. The actual longitudinal position for the distal end 16 of the elongated instrument 14 is determined using the determined longitudinal displacement for the distal end 26 of the elongated instrument 14 and the previous or initial longitudinal position of the distal end 26 of the elongated instrument 14, i.e. the determined longitudinal displacement for the distal end 26 is added to the initial displacement position of the distal end 26.

In one embodiment, the correction factor varies as a function of the length of the portion of the elongated instrument inserted into the medical apparatus 12 or the position of the distal end 26 of the elongated instrument 14 within the medical apparatus 12.

In one embodiment, the correction factor may decrease with the length of the portion of the elongated instrument inserted into the medical apparatus 12. As a result, the farther the distal end 16 of the elongated instrument is inserted into the medical apparatus 12, the less the adjustment factor is. This scenario allows simulating an increase of the buckling of the elongated instrument 14 as the elongated instrument 14 is more and more deeply inserted into the medical apparatus 12.

In one embodiment, the memory of the simulation computer machine 18 comprises a database containing respective values for the correction factor for different positions of the distal end 26 of the elongated instrument 14 within the medical apparatus 12.

It should be understood that the adjustment factor to be applied to the rotation angle of the proximal section of the elongated instrument in order to obtain the rotation angle to be applied to the distal end 26 of the elongated instrument 14 may be normalized so as to have values comprised between 0 and 1. When the adjustment factor is set to 0, then no rotation occurs for he distal end 26 of the elongated instrument 14 independently of the rotation angle applied to the proximal section of the elongated instrument 14. When the adjustment is set to 1, then the distal end 26 of the elongated instrument experiences the same rotation as the rotation of the proximal section of the elongated instrument. When the adjustment factor is set to a value between 0 and 1, the rotation angle applied to the distal end 26 of the elongated instrument 14 is less than the measured rotation angle of the proximal section thereof, thereby simulating torsion of the elongated instrument between the proximal section and the distal end 26.

It should be understood that the adjustment factor to be applied to the rotation angle of the proximal section of the elongated instrument in order to obtain the rotation angle to be applied to the distal end 26 of the elongated instrument 14 may be normalized so as to have values comprised between 0 and 1. When the adjustment factor is set to 0, then no rotation occurs for the distal end 26 of the elongated instrument 14 independently of the rotation angle applied to the proximal section of the elongated instrument 14. When the adjustment factor is set to 1, then the distal end 26 of the elongated instrument experiences the same rotation as the rotation of the proximal section of the elongated instrument. When the adjustment factor is set to a value between 0 and 1, the rotation angle applied to the distal end 26 of the elongated instrument 14 is less than the measured rotation angle of the proximal section thereof, thereby simulating torsion of the elongated instrument between the proximal section and the distal end 26.

Similarly to the adjustment factor for the rotation angle, it should be understood that the correction factor to be applied to the longitudinal displacement of the proximal section of the elongated instrument 14 in order to obtain longitudinal displacement to be applied to the distal end 26 of the elongated instrument 14 may be normalized so as to have values comprised between 0 and 1. When the correction factor is set to 0, then no longitudinal displacement occurs for the distal end 26 of the elongated instrument 14 independently of the longitudinal displacement applied to the proximal section of the elongated instrument 14. When the correction factor is set to 1, then the distal end 26 of the elongated instrument experiences the same longitudinal displacement as the longitudinal displacement of the proximal section of the elongated instrument. When the correction factor is set to a value between 0 and 1, the longitudinal displacement applied to the distal end 26 of the elongated instrument 14 is less than the measured longitudinal displacement of the proximal section thereof, thereby simulating bending of the elongated instrument between the proximal section and the distal end 26.

Figure 2:
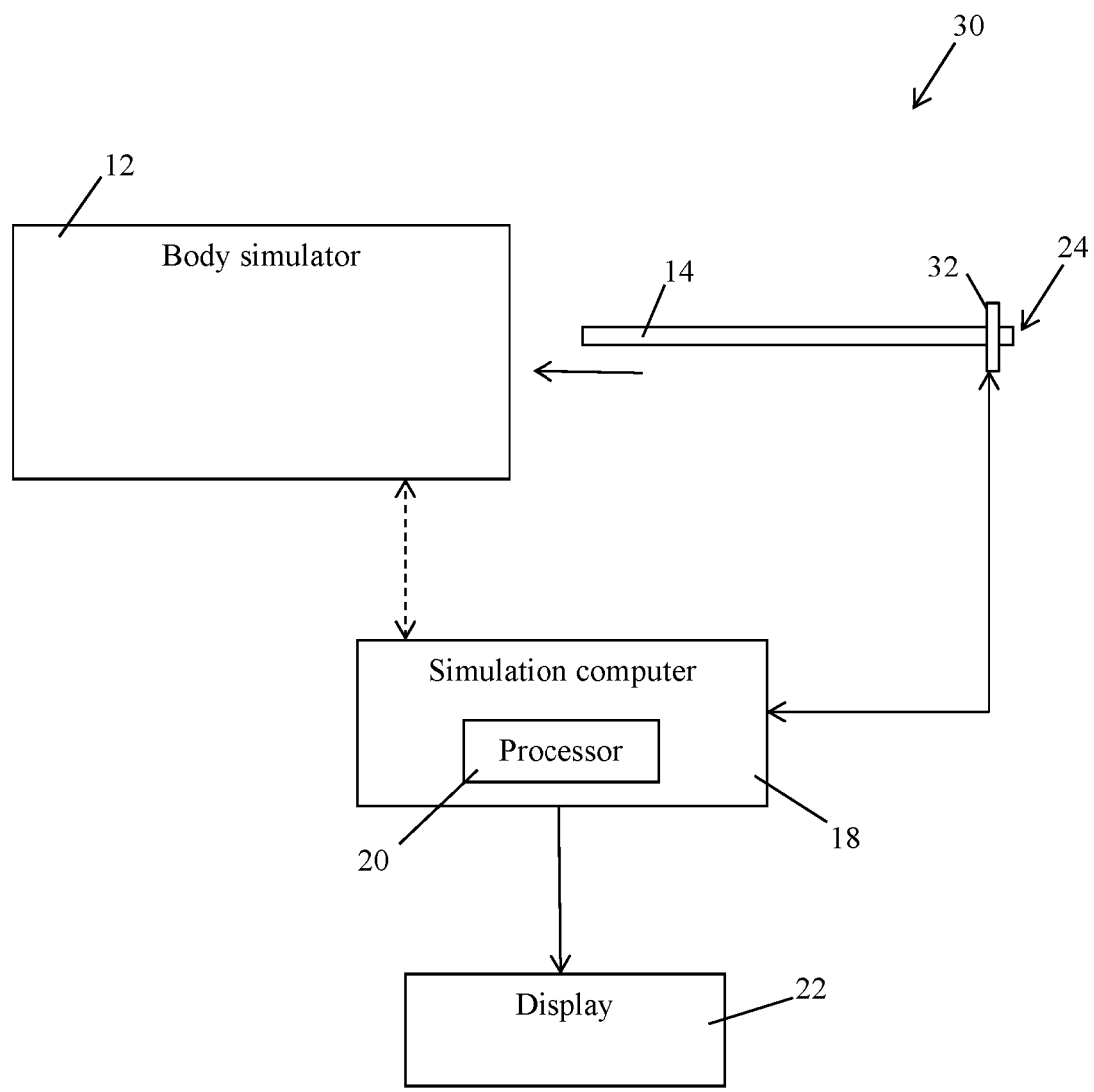
FIG. 2 is a block diagram illustrating a system comprising a sensing unit, an elongated instrument, an apparatus, a simulation machine and a display unit for simulating the insertion of the elongated instrument into a subject, in accordance with a second embodiment.

FIG. 2 schematically illustrates one embodiment of a system 30 for simulating the insertion of an elongated instrument into a subject. The system 30 comprises the same elements as those of the system 10 except for the sensing unit, i.e. the system 30 comprises the medical apparatus 12, the elongated instrument 14, the simulation computer 18 provided with the processing unit 20 and the display 22. The system 30 further comprises a sensing unit 32 secured to the proximal section of the elongated instrument 14. In the illustrated embodiment, the sensing unit 32 is positioned adjacent to the proximal end 24 of the elongated instrument 14. It should be understood that the sensing unit 32 may be removably secured to the elongated instrument 14. In this case, the position of the sensing unit 32 within the proximal section of the elongated instrument 14 may be changed. Alternatively, the sensing unit 32 may be permanently secured to the proximal section of the elongated instrument 14.

The sensing unit 32 may comprise at least one gyroscope for determining the angular position of the point of the proximal section to which it is secured or the angle of rotation about the longitudinal axis of the point of the proximal section to which it is secured.

In one embodiment, the sensing unit 32 may further comprise at least one accelerometer to measure the longitudinal position or displacement of the point of the proximal section to which it is secured.

In an embodiment in which the sensing unit 16, 32 is configured for measuring only the angular position or the rotation angle for the proximal section of the elongated instrument 14, the subjectmedical apparatus 12 may comprise a positon tracking device for tracking the position or the displacement of the distal end 24 of the elongated instrument 14 within the medical apparatus 12. It should be understood that any adequate position tracking device may be used. In this case, the position tracking device may be configured for transmitting the longitudinal position of the distal end 26 of the elongated instrument 14 to the simulation computer machine 18 in order to generate the medical image. The representation of the distal end 26 of the elongated instrument 14 within the generated image is made according to the longitudinal position determined by the position tracking device, in addition to determined angular position determined for the distal end 26 by the processing unit 20 of the simulation computer machine 18.

It should be understood that the medical apparatus 12 may be designed to simulate an artery or a vein in which the elongated instrument 14 is to be inserted and optionally an organ to he treated.

In one embodiment, the system 10, 30 is configured for training a medical practitioner to minimally invasive medical procedures. A minimally invasive medical procedure or surgery involves a small incision formed on the skin of the body of a subject through which an elongated instrument such as a guidewire or a catheter is inserted. The elongated instrument is then displaced within blood vessels such as arteries or veins to reach an organ to be treated. The person skilled in the art will understand that the system 30, 32 will assist medical practitioners to train for various minimally invasive procedures such as endoscopy, laparoscopy, arthroscopy and the like.

Figure 3:
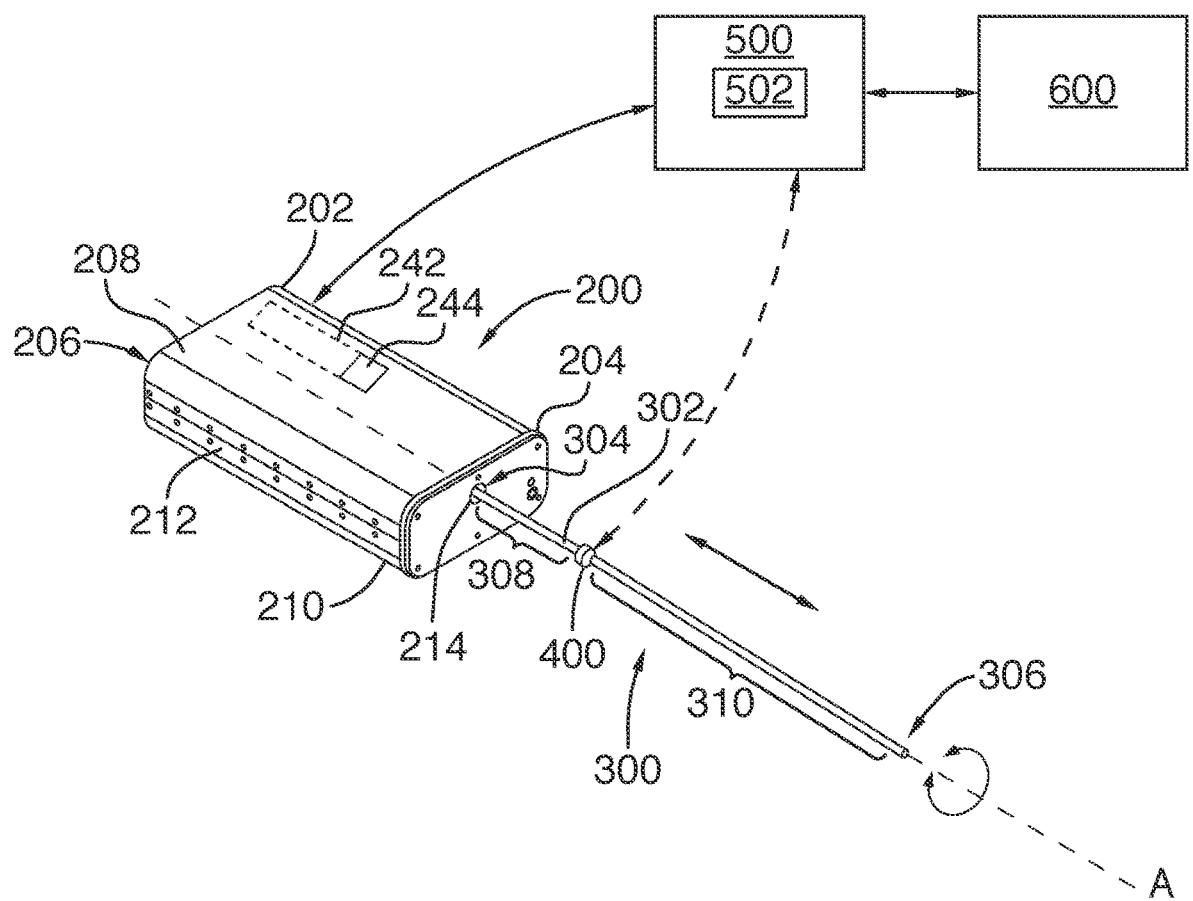
FIG. 3 illustrates a system comprising a sensing unit, an elongated instrument, an apparatus, a simulation machine and a display unit for simulating the insertion of the elongated instrument into a subject, in accordance with a third embodiment.
Figure 4:
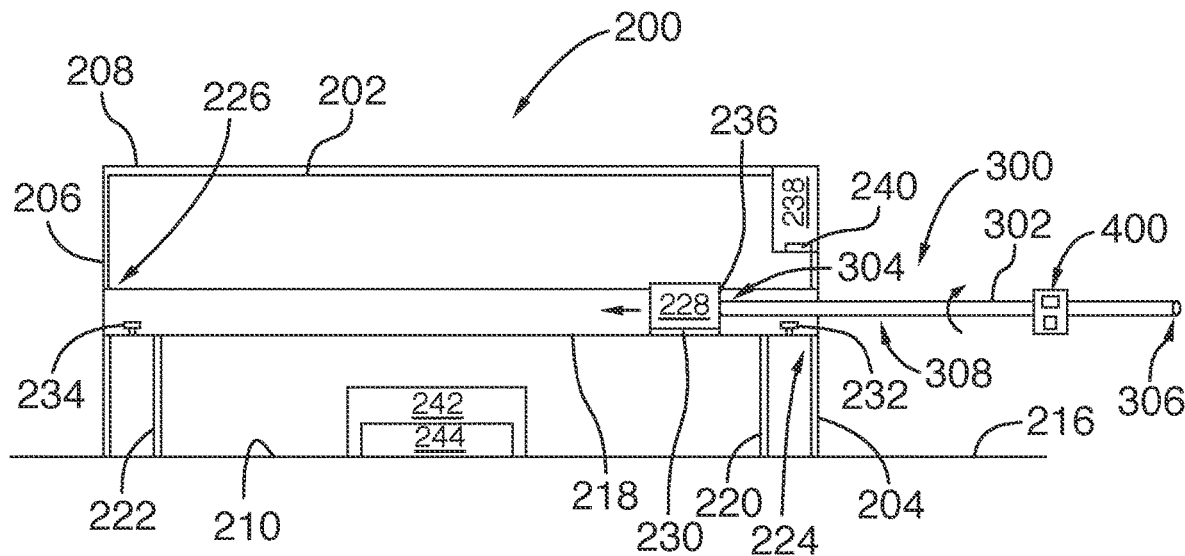
FIG. 4 is a cross-sectional view of the apparatus of FIG. 3, in accordance with an embodiment.

FIGS. 3 and 4 illustrates an exemplary system 100 for simulating the insertion of an elongated instrument into a subject. The system comprises a medical apparatusmedical or body simulating apparatus 200, an elongated instrument 300, a sensing unit 400, a simulation computer machine 500 and a display unit 600. In this embodiment, the sensing unit 400 is not configured for determining the longitudinal position of the proximal section of the elongated instrument 300 and the apparatus 200 is configured to measure the position of the distal end of the elongated instrument 300, as described below.

In one embodiment, the apparatus 200 comprises a frame 202 having a generally rectangular shape longitudinally extending between a proximal face 204 and a distal face 206 along a longitudinal axis A. The frame 202 further comprises a top face 208 removably secured to a bottom face 210 and defining a closed enclosure.

In one embodiment, the top face 208 may be removably secured to the bottom face 210 via a pair of slides 212 for providing access to the enclosure of the frame 202. In this embodiment and in order to gain access to the enclosure, the top face 208 may be removed from the apparatus 200 by sliding the top face 208 relative to the bottom face 210 along the longitudinal axis A. The person skilled in the art will understand that other mounting methods for mounting the top face 208 to the bottom face 210 may be contemplated for providing access to the enclosure. For instance, the top face 208 may be hinged to the bottom face 210 at a first side and may rotate around the axis of the hinge for providing access to the enclosure of the frame 202.

In one embodiment, the proximal face 204 has a generally rectangular shape and comprises an aperture 214 sized and shaped to receive the elongated instrument 300 therethrough. In one embodiment, the size of the aperture 214 may substantially correspond to the size of an incision made on a subject during a specific surgical procedure.

In one embodiment, various additional apertures may be provided, on the frame 202, for instance on the distal face 206 or on the top and bottom faces 208 and 210 for power and electronics communication with the simulation machine 500.

In one embodiment, the apparatus is disposed on a plane receiving surface 216 such as a table or a counter. For instance, the apparatus 200 may be positioned on a surgical table at an appropriate height from the floor surface for enabling a medical practitioner to train in similar condition as a real surgical procedure on a subject.

In one embodiment, the apparatus 200 further comprises a longitudinal guide rail 218 secured to the bottom face 210 of the frame 202 via support members 220 and 222, and extending along the longitudinal axis A of the apparatus 200 between a first end 224 joining the proximal face 204 and a second end 226 joining the distal face 206. The longitudinal guide rail 218 is further configured to be longitudinally aligned with the aperture 214.

In one embodiment, the longitudinal guide rail 218 comprises either a rail, a pair of rails, a channel, a tunnel, or any other type of structure, which can act as a longitudinal guide.

In one embodiment, the apparatus 200 further comprises a carriage 228 slidably mounted onto a longitudinal guide rail 218 for translation therealong. In the illustrated embodiment, the carriage 228 has a base plate 230 configured to slide freely onto the longitudinal guide rail 218 between a first abutting element 232 mounted at the first end 224 of the guide rail 218 and a second abutting element 234 mounted at the second end 226 of the guide rail 218. The first and second abutting elements 232 and 234 confine the movement of the carriage 228 along the elongated guide rail 218 within an operational range, i.e. the distance between the first and second abutting elements 232 and 234, corresponding for example to a distance of insertion of the elongated instrument within the subject to reach the organ to be treated for a specific surgical procedure.

In one embodiment, the longitudinal guide rail 218 may comprise a plurality of holes (not shown) equally spaced therealong and sized and shaped to receive the first and second abutting elements 232 and 234. Therefore, according to the type of surgical procedure to be simulated, the operational range may be modified by removably positioning the first and second abutting elements 232 and 234 at different holes of the guide rail 218 to better reflect a given surgical procedure.

In one embodiment, the carriage 228 comprises a face 236 aligned with the aperture 214 for receiving a distal end 304 of the elongated instrument 300 when inserted therethrough. The distal end 304 of the elongated instrument 300 is then removably secured to the carriage 228. As it will be explained in more details below, upon further insertion of the elongated instrument 300 within the apparatus 200 through the aperture 214, the elongated instrument 300 is linearly displaced along the longitudinal guide rail 218 by abutting against the face 236 of the carriage 228.

In one embodiment, the apparatus 200 may further comprise a carriage position sensing element 238 and a linear encoder strip (not shown) mounted along the elongated guide rail 218, and a corresponding optical reader 240 as shown in FIG. 4 for example, is used for sensing a longitudinal position of the carriage 228 along the longitudinal guide rail 218 during displacement of the elongated instrument 300. The person skilled in the art will understand that other linear position tracking devices may be used for measuring the displacement of the carriage 228, such as an accelerometer, a capacitive transducer, a capacitive displacement sensor, an Eddy-current sensor, a Hall effect sensor, an inductive non-contact position sensor or the like. In another embodiment, it should further be understood that different adequate methods and techniques for determining the displacement of the carriage 228 may be used.

In one embodiment, the apparatus 200 may further comprise a feedback force actuator (not shown) adapted to apply a resistive force to the longitudinal displacement of the carriage 228 along the guide rail 218 for providing an enhanced and realistic displacement of the elongated instrument 300 when inserted in the apparatus 200. The feedback force actuator may for instance comprise a motor (not shown), such as a stepper motor, secured to the carriage 228, a control unit (not shown) and a transmission element (not shown) coupled to the motor and the control unit. The feedback force actuator may be controlled by the control unit according to the longitudinal displacement of the carriage 228 and the resistance characteristics of the subject's body. The resistance characteristics of the body are representative of a subject's internal structure into which the elongated instrument 300 is to be inserted. These resistance characteristics may be provided by a specific 3D model of a structure of a specific subject and may embed natural movements of a human body like heart beating and breathing. For instance, these characteristics may include tissue resistance during insertion of the elongated instrument 300 within an artery or a vein.

In one embodiment, the resistance characteristics are adjusted by the control unit depending on a given surgical procedure for enabling medical practitioner trainees to train with hands-on conditions substantially similar to real surgery.

In one embodiment, the apparatus 200 further comprises an electronic unit 242 operatively coupled to the carriage position sensing element 238 and the control unit of the feedback actuator. The electronic unit 242 comprises a communication unit 244 configured to communicate to the simulation machine 500 the measured displacement values of the carriage 228 as well as the resistance characteristics applied by the control unit.

In one embodiment, the electronic unit 242 of the apparatus 200 is wired to the simulation machine 500 using communication cables. In an alternative embodiment, the electronic unit 242 is wirelessly connected to the simulation machine 500 using wireless protocols such as WiFi, Bluetooth® and the like.

As illustrated in FIGS. 3 and 4, the sensing unit 400 is mounted on the elongated instrument 300.

In one embodiment, the elongated instrument 300 is a medical grade surgical instrument used in minimally invasive procedures. The elongated instrument 300 may be a catheter, a lead wire, a delivery tube or a guidewire adapted to be inserted into a subject and displaced through an artery or vein to reach an organ to be treated. For instance, the elongated instrument 300 may be used for different surgical procedures such as cardiovascular, urological, gastrointestinal, neurovascular, ophthalmic procedures and the like.

In one embodiment, the elongated instrument 300 has a generally elongated shape comprising a tubular body 302 extending longitudinally between a distal end 304 insertable in the apparatus 200 through the aperture 214 and a proximal end 306, located away from the apparatus 200. The elongated instrument 300 may further be segmented into a distal section 308 extending from the distal end 304 and configured to be inserted in the apparatus 200 and a proximal section 310 extending from the proximal end 306 and adapted to remain outside of the apparatus 200. In this case, the distal section 308 corresponds at least to the operational range of displacement of the carriage 228 along the guide rail 218. The sensing unit 400 is secured to the proximal section 310 of the elongated member 300. In the present embodiment, the sensing unit 400 is removably secured to the elongated instrument 300.

Figure 5:
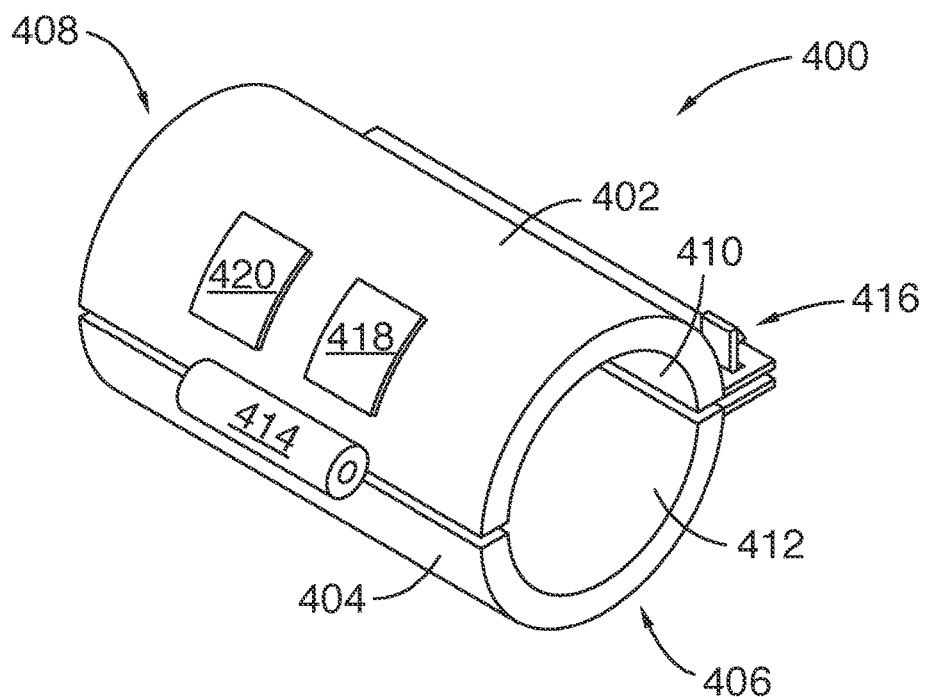
FIG. 5 is a perspective view of the sensing unit of FIG. 3, in accordance with an embodiment.

As illustrated in FIG. 5, the sensing unit 400 has a generally longitudinal cylindrical shape comprising a first hemi-tubular section 402 and a second hemi-tubular section 404 extending longitudinally between a first end 406 and a second end 408. The first hemi-tubular section 402 has a semicircular shape and comprises a first internal surface 410 extending between the first end 406 and the second end 408. The second hemi-tubular section 404 has a semicircular shape, similar to the shape of the first hemi-tubular section 402, and comprises a second internal surface 412 extending form the first end 406 to the second end 408.

The first and second hemi-tubular sections 402 and 404 are hingedly coupled together via a hinge 414 and are adapted to move between an open configuration wherein the first and second hemi-tubular sections 402 and 404 are rotated away from each other and a closed configuration wherein the first and second hemi-tubular sections 402 and 404 are secured together via an attachment member 416 located diametrically away from the hinge 414.

In another embodiment, the first and second hemi-tubular sections 402 and 404 may further be coupled together using fasteners.

In one embodiment, the sensing unit 400 is adapted to be tightly clamped on the proximal section 310 of the elongated instrument 300, as shown in FIGS. 3 and 4. More precisely, as the sensing unit 400 is clamped on the proximal section 310 of the elongated instrument 300, the first and second internal surfaces 410 and 412 of the first and second hemi-tubular sections 402 and 404 are in friction engagement with the body 302 of the elongated instrument 300 therefore preventing relative movement therebetween.

In one embodiment, the sensing unit 400 comprises an sensor 418, located on either the first or second hemi-tubular sections 402 and 404 and configured to measure the angular position or the rotation angle of the proximal section 310 of the elongated instrument 300.

In one embodiment, the sensor 418 may be a gyroscope sensor such as a microelectromechanical system (MEMS) gyro sensor or a 3 axis gyro sensor adapted to measure the angular velocity of the proximal section 310 of the elongated instrument 300 during manipulation by the medical practitioner trainee.

The sensing unit 400 further comprises a communication unit 420 located in either the first or second hemi-tubular sections 402 and 404, and configured to communicate with the simulation machine 500 for transmitting the measured value to the proximal section 310 of the elongated instrument 300 thereto.

In one embodiment, the communication unit 420 may communicate with the simulation machine 500 either via wires or wirelessly using communication protocols such as WiFi, Bluetooth® and the like.

In use, the sensing unit 400 is clamped to the proximal section 310 of the elongated instrument 300 by securing an attachment member 416 between the first and second hemi-tubular sections 402 and 404. Once clamped onto the elongated instrument 300, the angular position or rotation about its axis of the proximal section 310 of the elongated instrument 300 is continuously measured by the sensing unit 400 and communicated to the simulation machine 500 via the communication unit 420.

It should be understood that the hinge 414 may be omitted and replaced by additional fasters. In this case, the first hemi-tubular section 402 and a second hemi-tubular section 404 are independent form one another.

I should be understood that when the sensing unit is securable to the elongated instrument, any adequate method for permanently or removably securing the sensing unit to the elongated instrument may be used. For example, the sensing unit may comprise a flexible and elastic tubular body acting as a sleeve or sheath to be positioned over the elongated instrument at an adequate position.

Figure 6:
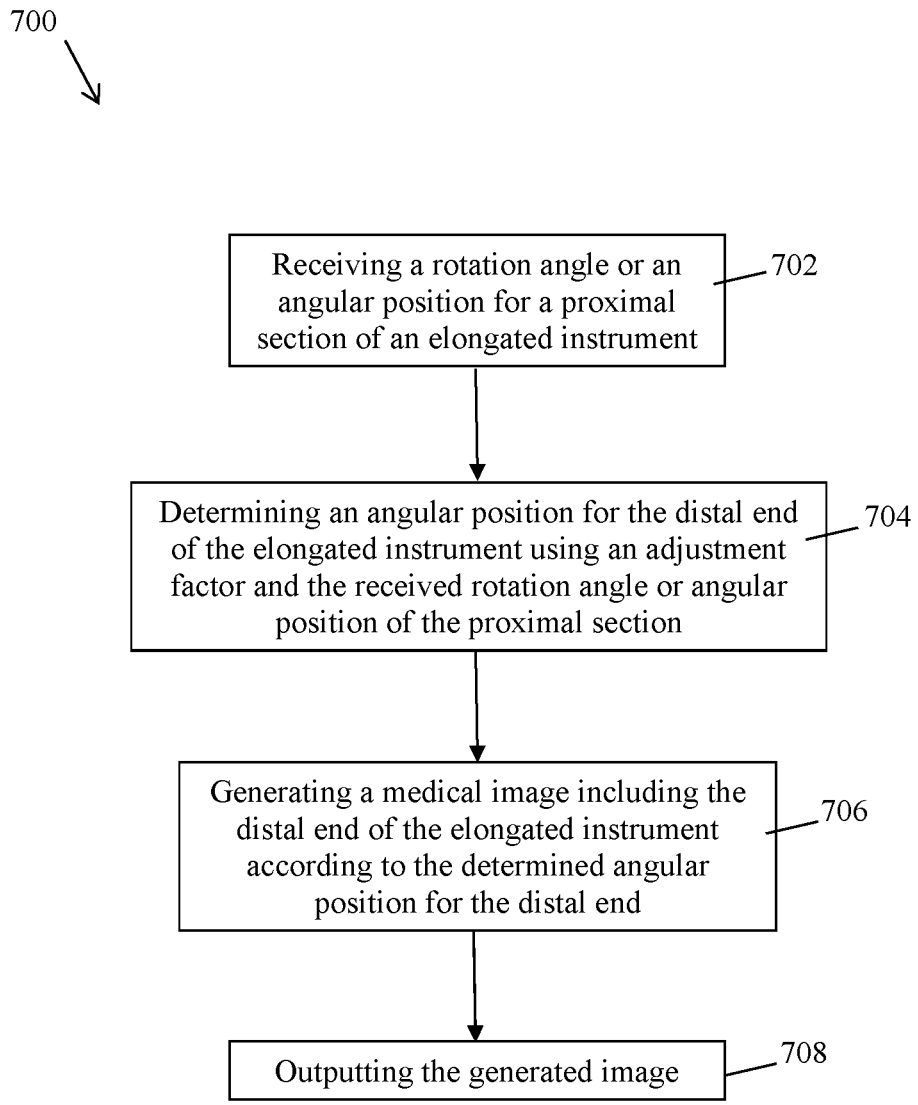
FIG. 6 is a flow chart of a method for simulating the insertion of an elongated instrument in a subject, in accordance with an embodiment.

FIG. 6 illustrates one embodiment of a computer-implemented method 700 for simulating the insertion of an elongated medical instrument into a subject. The method 700 is performed by a computer machine provided with a processing unit, a memory and communication means. The method 700 is performed in collaboration with a medical apparatus in which the distal end of an elongated instrument is inserted, as described above.

At step 702, the rotation angle or the angular position of the proximal section of the elongated instrument is received. As described above any adequate method for measuring the rotation angle of the proximal section of the elongated instrument about its axis or the angular position of the proximal section may be used.

At step 704, the angular position for the distal end of the elongated instrument is determined using an adjustment factor and the measured rotation angle or angular position of the proximal section of the elongated instrument received at step 702, as described above.

At step 706, a medical image of a portion of the subject is generated. The generated image comprises a representation of at least the distal end of the elongated instrument which is generated according to the angular position determined at step 704.

At step 708, the generated image is outputted. The generated image may be stored in memory and/or displayed on a display unit.

In one embodiment, the medical apparatus comprises a position tracking device which measures the longitudinal position of the distal end of the elongated instrument within the medical apparatus. In this case, the method 700 may further comprise a step of receiving the longitudinal position of the distal end of the elongated instrument and the generation of the medical image is performed according to the measured longitudinal position of the distal end of the elongated instrument.

In another embodiment, the method 700 further comprises a step of receiving a longitudinal position or a longitudinal displacement of the proximal section of the elongated instrument and a step of determining the longitudinal position for the distal end of the elongated instrument, as described above. In this case, the generation of the medical image is performed according to the determined longitudinal position for the distal end of the elongated instrument.

In one embodiment, the tracking of the angular position or rotation angle of the proximal section of the elongated instrument is performed substantially continuously. In this case, the steps 702-708 are performed substantially continuously to as a provide a real-time simulation.

Figure 7:
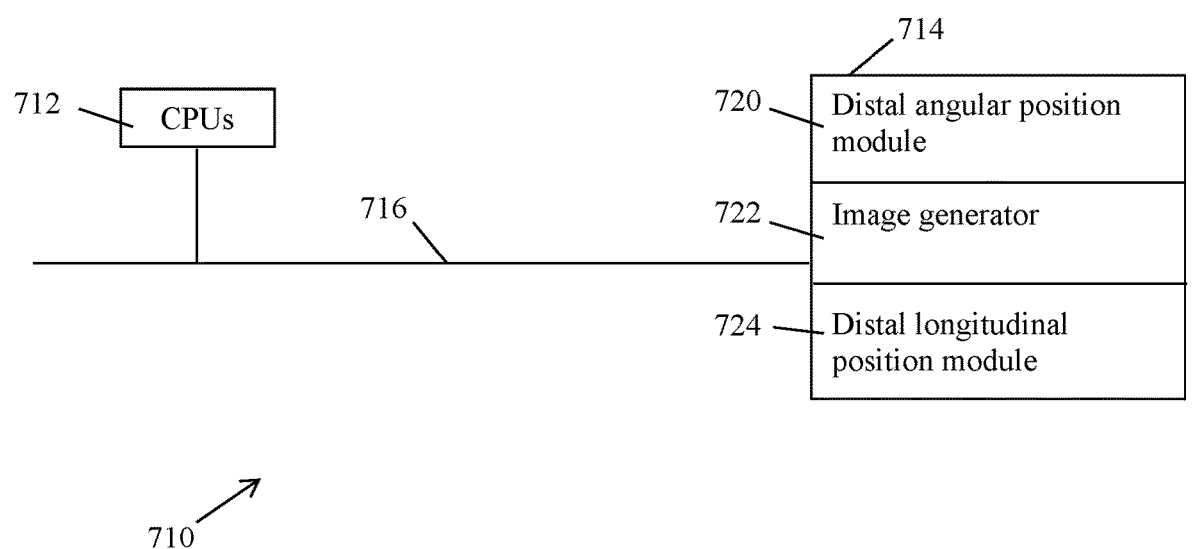
FIG. 7 is a block diagram of a processing module adapted to execute at least some of the steps of the method of FIG. 1, in accordance with an embodiment.

FIG. 7 is a block diagram illustrating an exemplary processing module 710 for executing the steps 702 to 708 of the method 10, in accordance with some embodiments. The processing module 710 typically includes one or more Computer Processing Units (CPUs) and/or Graphic Processing Units (GPUs) 712 for executing modules or programs and/or instructions stored in memory 714 and thereby performing processing operations, memory 714, and one or more communication buses 716 for interconnecting these components. The communication buses 716 optionally include circuitry (sometimes called a chipset) that interconnects and controls communications between system components. The memory 714 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 714 optionally includes one or more storage devices remotely located from the CPU(s) 712. The memory 714, or alternately the non-volatile memory device(s) within the memory 714, comprises a non-transitory computer readable storage medium. In some embodiments, the memory 714, or the computer readable storage medium of the memory 714 stores the following programs, modules, and data structures, or a subset thereof:

a distal angular position module 720 calculating the angular position for the distal end of the elongated instrument using an adjustment factor and the measured rotation angle or angular position for the proximal section of the elongated instrument, as described above;

an image generator 722 generating a medical image of a portion of a subject comprising a presentation of the distal end of the elongated instrument according to the angular position determined for the distal end of the elongated instrument; and a distal longitudinal position module 724 calculating the longitudinal position of the distal end of the elongated instrument using a correction factor and the measured longitudinal displacement or longitudinal position for the proximal section of the elongated instrument, as described above.

It should be understood that the distal longitudinal position module 724 may be omitted.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, the memory 714 may store a subset of the modules and data structures identified above. Furthermore, the memory 714 may store additional modules and data structures not described above.

Although it shows a processing module 710, FIG. 7 is intended more as functional description of the various features which may be present in a management module than as a structural schematic of the embodiments described herein. In practice, and as recognized by those of ordinary skill in the art, items shown separately could be combined and some items could be separated.

The embodiments described above are intended to be exemplary only. The scope of the invention is therefore intended to be limited solely by the appended claims.

We claim:

1. A system for simulating an insertion of an elongated instrument into a subject, the system comprising:
a medical apparatus comprising a frame extending between a proximal face and a distal face along a longitudinal axis, the proximal face being provided with an aperture for receiving an elongated instrument therein;
a sensing unit being configured to measure one of an actual angular position and a rotation angle for a proximal section of the elongated instrument when the elongated instrument is inserted at least partially into the aperture of the medical apparatus; and
a simulation machine in communication with the sensing unit, the simulation machine comprising at least a processing unit configured for:
calculating a distal angular position for a distal end of the elongated instrument using an adjustment factor and the one of the actual angular position and the rotation angle for the proximal section of the elongated instrument, the adjustment factor being chosen so as to simulate a torsion of the elongated instrument between the proximal section thereof and the distal section thereof;
generating a medical image of at least a portion of the subject, the medical image comprising at least a representation of a distal section of the elongated instrument, the representation of the distal section being generated according to the distal angular position; and
providing the generated medical image for display.

2. The system of claim 1, wherein the sensing unit is adapted to measure the actual angular position of the proximal section of the elongated instrument, the processing unit being further configured for determining the rotation angle based on the actual angular position and an initial angular position for the proximal section of the elongated instrument.

3. The system of claim 1, wherein the sensing unit is securable to the proximal section of the elongated instrument.

4. The system of claim 3, wherein the sensing unit comprises a tubular section securable over a portion of the proximal section of the elongated instrument.

5. The system of claim 4, wherein the sensing unit comprises a first hemi-tubular section and a second hemi-tubular section securable together over the elongated instrument.

6. The system of claim 3, wherein the sensing unit comprises at least one gyroscope sensor for measuring the one of the actual angular position and the rotation angle for the proximal section of the elongated instrument.

7. The system of claim 1, wherein the adjustment factor varies as a function of a position of the distal end of the elongated instrument within the medical apparatus.

8. The system of claim 1, wherein the sensing unit is further configured for measuring one of an actual longitudinal position and a longitudinal displacement for the proximal section of the elongated instrument, the processing unit being further configured for:
calculating a distal longitudinal position for the distal end of the elongated instrument using a correction factor and the one of the actual longitudinal position and the longitudinal displacement for the proximal section of the elongated instrument, the correction factor being chosen so as to simulate a bending of the elongated instrument between the proximal section thereof and the distal section thereof; and
generating the medical image taking into account the distal longitudinal position for the distal end of the elongated instrument, and, wherein the sensing unit is configured for measuring the actual longitudinal position of the proximal section of the elongated instrument and the processing unit is further configured for determining the longitudinal displacement for the proximal section of the elongated instrument using the actual longitudinal position and an initial longitudinal position for the proximal section of the elongated instrument.

9. The system of claim 8, wherein the sensing unit further comprises at least one accelerometer for measuring the one of the actual longitudinal position and the longitudinal displacement for the proximal section of the elongated instrument.

10. The system of claim 8, wherein the correction factor varies as a function of a position of the distal end of the elongated instrument within the medical apparatus.

11. The system of claim 1, wherein the elongated instrument is selected from a group consisting of a catheter, a lead wire, a delivery tube and a guidewire.

12. The system of claim 1, wherein the medical apparatus further comprises a longitudinal guide secured within the frame, the longitudinal guide extending between the proximal face and the distal face along the longitudinal axis for receiving and guiding the distal end of the elongated instrument upon insertion through the aperture of the proximal face.

13. The system of claim 1, wherein the medical apparatus comprises a position sensor for measuring one of a longitudinal position and a displacement for the distal end of the elongated instrument within the frame and the at least a processing unit being configured for generating the medical image taking into account the one of the longitudinal position and the displacement for the distal end of the elongated instrument.

14. The system of claim 1, wherein the processing unit is configured for at least one of storing the generated medical image into a memory and transmitting the generated medical image to a display unit to be displayed thereon and wherein the sensing unit comprises a wireless communication unit for wirelessly transmitting at least the measured angular position to the simulation machine.

15. A computer-implemented method for simulating an insertion of an elongated instrument into a subject, the method being executed by a processor, the processor being connected to a sensing unit and to a display unit, the method comprising:
communicatively coupling said processor to said sensing unit through a communication unit for transmitting and receiving data;
detecting at a sensing unit an insertion of at least a distal end of an elongated instrument into a medical apparatus, the medical apparatus comprising a frame extending between a proximal face and a distal face along a longitudinal axis, the proximal face being provided with an aperture for receiving the elongated instrument therein;
receiving, from the sensing unit, one of an actual angular position and a rotation angle for a proximal section of the elongated instrument inserted into the medical apparatus;
determining a distal angular position for the distal end of the elongated instrument inserted into the medical apparatus using an adjustment factor and the one of the actual angular position and the rotation angle for the proximal section of the elongated instrument, the adjustment factor being chosen so as to simulate a torsion of the elongated instrument between the proximal section thereof and the distal section thereof when the actual angular position is measured;
generating a medical image of at least a portion of the subject, the medical image comprising at least a representation of a distal section of the elongated instrument, the representation of the distal section being generated according to the distal angular position; and
providing the generated medical image for display on the display unit.

16. The method of claim 15, wherein said receiving the one of the actual angular position and the rotation angle comprises receiving the actual angular position of the proximal section of the elongated instrument, the method further comprising determining the rotation angle using the actual angular position and an initial angular position for the proximal section of the elongated instrument.

17. The method of claim 15, wherein a value of the adjustment factor depends on a position of the distal end of the elongated instrument within the medical apparatus.

18. The method of claim 15, further comprising receiving one of an actual longitudinal position and a longitudinal displacement for the proximal section of the elongated instrument and calculating a distal longitudinal position for the distal end of the elongated instrument using a correction factor and the one of the actual longitudinal position and the longitudinal displacement for the proximal section of the elongated instrument, the correction factor being chosen so as to simulate a bending of the elongated instrument between the proximal section thereof and the distal section thereof; said generating the medical image being performed taking into account the distal longitudinal position for the distal end of the elongated instrument, and wherein said receiving the one of the actual longitudinal position and the longitudinal displacement comprises receiving the actual longitudinal position, the computer-implemented method further comprising determining the longitudinal displacement for the proximal section of the elongated instrument using the actual longitudinal position and an initial longitudinal position for the proximal section of the elongated instrument.

19. The method of claim 18, wherein said receiving the one of the actual longitudinal position and the longitudinal displacement comprises receiving at least one acceleration value, the computer-implemented method further comprising determining the one of the actual longitudinal position and the longitudinal displacement from the at least one acceleration value.

20. The method of claim 18, wherein a value of the correction factor depends on a position of the distal end of the elongated instrument within the medical apparatus.

21. A method for simulating an insertion of an elongated instrument into a subject, the method comprising:
  measuring, by a sensing unit, one of an actual angular position and a rotation angle for a proximal section of an elongated instrument while the elongated instrument has at least a distal end inserted into a medical apparatus, the medical apparatus comprising a frame extending between a proximal face and a distal face along a longitudinal axis, the proximal face being provided with an aperture for receiving the elongated instrument therein;
  determining a distal angular position for the distal end of the elongated instrument inserted into the medical apparatus using an adjustment factor and the one of the actual angular position and the rotation angle for the proximal section of the elongated instrument, the adjustment factor being chosen so as to simulate a torsion of the elongated instrument between the proximal section thereof and the distal section thereof when the actual angular position is measured;
  generating a medical image of at least a portion of the subject, the medical image comprising at least a representation of a distal section of the elongated instrument, the representation of the distal section being generated according to the distal angular position; and
  providing the generated medical image for display on the display unit.

22. A computer readable medium comprising program instructions stored thereon, wherein execution of the program instructions by one or more processors of a computer system causes the one or more processors to carry out the steps of the method claim 21.

* * * * *